United States Patent [19]

Chan

[11] 4,187,611
[45] Feb. 12, 1980

[54] DENTAL RETENTION PIN AND METHOD
[75] Inventor: Kai C. Chan, Iowa City, Iowa
[73] Assignee: University of Iowa Research Foundation, Iowa City, Iowa
[21] Appl. No.: 840,280
[22] Filed: Oct. 7, 1977
[51] Int. Cl.² .............................................. A61C 5/00
[52] U.S. Cl. .................................................. 433/225
[58] Field of Search ............ 32/15, 6, 7, 10 A, 10 R; 85/42

[56] References Cited

U.S. PATENT DOCUMENTS

| 2,609,604 | 9/1952 | Sprague | 32/10 A |
| 3,395,455 | 8/1968 | Overby et al. | 32/6 |
| 3,434,209 | 3/1969 | Weissman | 32/15 |
| 3,579,831 | 5/1971 | Stevens et al. | 32/10 A |
| 3,672,058 | 6/1972 | Nikoghossian | 32/10 A |
| 3,675,328 | 7/1972 | Weissman | 32/15 |
| 3,675,329 | 7/1972 | Weissman | 32/15 |
| 3,861,043 | 1/1975 | Lieb et al. | 32/15 |
| 3,905,109 | 9/1975 | Cohen et al. | 32/10 A |
| 3,934,347 | 1/1976 | Lash et al. | 32/10 A |

OTHER PUBLICATIONS

"Leakage Around Various Types of Retention Pins", Chan et al., J. Prosthetic Dent., 33:191-194, 2-75.
"Influence of Varnish on Microleakage and Retention...", Moffa et al., J. Prosthetic Dent., 20:540-551, 1968.
"The Adaptation of Noncemented Pins", Perez et al., J. D. Prosth., 26:631-639, 12-1971.

Primary Examiner—Russell R. Kinsey
Assistant Examiner—John J. Wilson
Attorney, Agent, or Firm—Quaintance, Murphy & Richardson

[57] ABSTRACT

A dental retention pin has a threaded longitudinally grooved lower shaft section, an intermediate sealing section for sealing the hole in which the pin is threaded, and an upper section embeddable in a surrounding body of restorative material. A pinhole is drilled in a tooth and the pin is inserted therein by rotation to cut threads in the dentin as fluids are vented through the groove. The sealing section then enters the pinhole to establish a sealing relationship therewith.

5 Claims, 5 Drawing Figures

DENTAL RETENTION PIN AND METHOD

BACKGROUND AND SUMMARY OF THE INVENTION

This invention pertains to threaded retention pins used in restorative dentistry for enhancing the attachment of an amalgam or other restorative material on the tooth. Well known retention pins of this general type are externally threaded and are inserted by rotation into a previously-drilled pinhole which extends into the dentin of the tooth structure. Rotation of such a pin cuts internal threads in the pinhole and advances the pin longitudinally into the pinhole. When the pin is sufficiently inserted, a driving head at the upper end thereof is sheared from the pin by a self-shearing joint, leaving an upper portion of the retention pin in the restoration cavity where the restorative material is placed thereabout.

I have recognized heretofore that retention pins which do not have thread cutting edges produce crazing of the dentin. This is averted to some extent by the structure shown by thread cutting U.S. Pat. No. 3,861,043 in which edges are provided at the extreme lower end of a short slot retention pin. I have informed others in publications made in 1973 and 1974 that crazing would be reduced by a retention pin resembling a machinist's tap, having peripheral threads interrupted by longitudinal grooves. The present invention pertains to improvements in such proposed retention pins, such improvements pertaining in part to the provision in the pin of a pinhole-sealing section which seals against the interior wall of the pinhole and substantially prevents the entry of fluid into the groove or grooves located within the pinhole. The invention also pertains to a method of preparing a restoration cavity by the use of such an improved retention pin.

This invention has as its objectives the provision of a retention pin and method of use which reduces the crazing of the dentin while at the same time becoming affixed securely to the tooth and preventing the entry of fluids into the pinhole once the retention pin is in position.

According to this invention, the retention pin includes an externally threaded lower shaft having a vent passage for releasing fluid from the pinhole as the lower shaft portion is inserted. A pinhole sealing portion is located at the upper end of the lower shaft portion and has a peripheral sealing surface which engages the pinhole surface to prevent fluid from entering the pinhole when the lower shaft portion is fully inserted in the pinhole. An upper shaft portion extends upwardly from the pinhole-sealing portion for embedment in restorative material placed in the restoration cavity.

The method of this invention involves the drilling of a pinhole of a given diameter, inserting an externally threaded lower end of a retention pin in the pinhole by rotation, the lower end being provided with threads having a crest diameter greater that the pinhole diameter. During such rotation, fluid is vented from the pinhole to prevent compression, and threads are cut in the pinhole by moving thread-cutting edges on the pin into the wall of the pinhole. During the final stages of the insertion step, a sealing portion of the pin is moved into the pinhole, such sealing portion having a diameter substantially equal to the pinhole diameter.

For a more complete understanding of this invention, reference is made to the accompanying drawings and the following description of a preferred embodiment.

DESCRIPTION OF A PREFERRED EMBODIMENT

Figure 1:
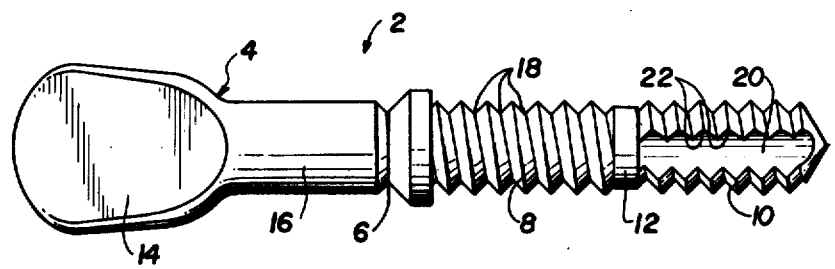
FIG. 1 is a view of a retention pin constructed according to the invention.

The retention pin assembly 2 of FIG. 1 is a single member formed of stainless steel, gold plated to resist corrosion and to achieve better adhesion to dental amalgams. The assembly includes a head 4 connected by a self shearing joint 6 to a shaft which includes an upper portion 8 and a lower portion 10, the shaft portions 8 and 10 being separated by a sealing and stabilizing portion 12.

The head 4 is used only during installation of the pin and is removed by torsional failure at the joint 6 when the pin is driven home to its final position. The upper end of the head 4 is flattened at 14, machined to fit into a special hand wrench or the chuck of a reduced speed contra-angle hand piece. The shank 16 extends downwardly from the flattened portion 14 to the self shearing joint 6 which is of a reduced diameter providing a lesser resistance at this point to torsional shear forces that in the remainder of the dental retention pin. As will be explained below, when the pin arrives at its final desired position shown in FIG. 4, it can rotate no further, therefore subjecting the self shearing joint 6 to torsional forces which cause it to break, leaving only the portions 8, 10 and 12 attached to the tooth.

Figure 4:
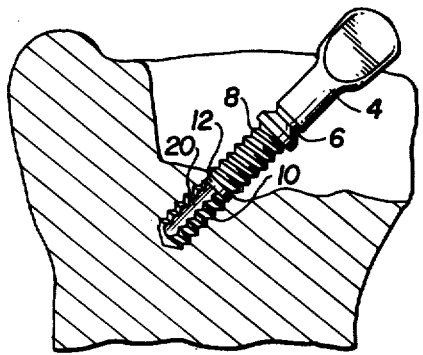
FIG. 4 shows the retention pin in its final position.

When attached to the tooth as shown in FIG. 4, the lower shaft portion 10 is anchored within the dentin, the sealing and stabilizing portion 12 is also within the pinhole formed in the dentin, and the upper shaft portion 8 extends upwardly into the restoration cavity for embedment in restorative material placed thereabout.

The upper shaft portion 8 is provided with helical grooves which serve as recesses 18 which ultimately are filled by the restorative material and promote mechanical engagement between the upper shaft portion 8 and the restorative material. Such recesses may be provided by a wide variety of undercut configurations applied to the upper shaft portion 8.

The lower shaft portion 10 has external helical threads for engaging the dentin both in the course of installation and use of the pin. To prevent crazing of the dentin and to enable air or liquid to escape from the pinhole during pin installation, the lower shaft portion 10 is provided with one or more vent passages 20 having a length of at least 1.5 mm. The vent passage 20 is a longitudinal groove which extends through the crests of the threads on the lower shaft portion 10, also providing cutting edges 22 for cutting internal threads in the dentin during rotation of the pin. The lower end of the shaft portion 10 is tapered to conform to the configuration of the bottom of the pinhole bore formed in the tooth by a twist drill having a tapered lowered end.

The sealing and stabilizing portion 12 lies between the upper shaft portion 8 and lower shaft portion 10. It has a peripheral sealing surface, preferably of smooth cylindrical configuration, having a diameter substantially the same as that of the pinhole previously drilled in the tooth. It serves to engage the pinhole surface to prevent fluid from entering the pinhole when the lower shaft portion 10 is fully inserted in the pinhole. The diameter of the sealing portion 12 is less than the crest diameter of the threads on the lower shaft portion 10, and is preferably of a diameter greater than the root diameter of the threads on portion 10.

In a representative device, the head 4 has a length of 4.0 mm with the shank 16 having a diameter of 0.60 mm. The upper shaft portion 8 has a length of 2.0 mm and a diameter of 0.60 mm. The sealing and stabilizing collar 12 has a diameter of 0.50 mm and a length of 0.2 mm, while the thread cutting lower shaft portion 10 has a length of 2.0 mm and a diameter of 0.60 mm.

Figure 2:
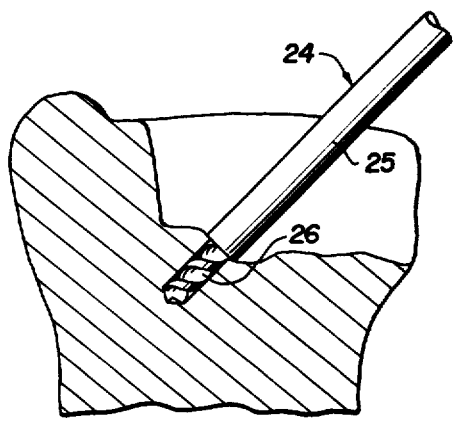
FIG. 2 shows the drilling of a tooth preparatory to installation of a retention pin therein.

The installation of the improved dental retention pin is illustrated in FIGS. 2-5. FIG. 2 shows the step of drilling into the dentin with a twist drill 24 having an enlarged shank 25, a conventional helically-fluted section 26 of a diameter equal to the resulting pinhole diameter, and a conical or tapered lower end provided with the cutting surfaces as is conventional in drill bits of this type. The drill should be made of carbide steel, and may have a total length of 20 mm. The drill shank may have a diameter of 2.4 mm and the fluted and conical portion may have a length of 2.2 mm and a diameter of 0.50 mm. The size should be small enough for use in anterior teeth and strong enough for use in molars.

Figure 3:
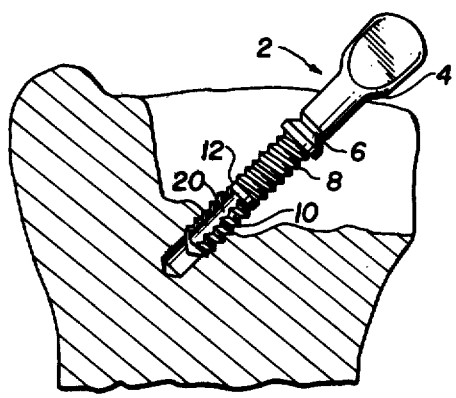
FIG. 3 shows an early stage of insertion of a retention pin into the tooth.
Figure 5:
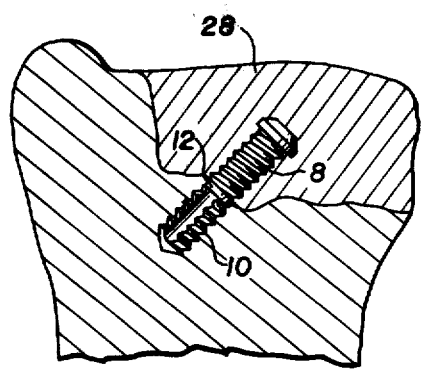
FIG. 5 shows the structure of FIG. 4 after the addition thereto of an amalgam or other restorative material.

The pinhole left by the drill bit has cylindrical sidewalls and a conical lower end formed by the tapered forward portion of the drill bit. The retention pin is inserted in the pinhole by aligning it longitudinally with the axis of the pinhole and then manually or mechanically rotating the pin about its longitudinal axis, causing the threads on the lower shaft portion to advance the pin downwardly into the pinhole. As the pin advances as shown in FIG. 3, air or liquid in the pinhole is permitted to escape through the vent 20. The cutting edges 22 which extend along the lower shaft portion 10 cut into the dentin in a manner which produces less crazing than prior retention pins which lack such a passage 20. Eventually, the lower shaft portion 10 is located entirely within the pinhole with its lower tapered conical surface conforming to the tapered lower end of the pinhole to minimize any fluid inclusions. At this position, illustrated in FIG. 4, the sealing and stabilizing portion 12 is also located in the pinhole, the cylindrical outer surface of the portion 12 conforming to the wall of the pinhole to seal the pinhole and prevent materials from entering the vent passage 20. As the shaft portions 8 and 10 at this point can rotate no further, continued imposition of rotational forces to the head 4 will cause torsional shearing to occur at the self shearing joint 6, disconnecting the head from the remainder of the device. Then, as shown in FIG. 5, a restorative material 28 is placed in the restoration cavity, surrounding the upper shaft portion 8 and projecting into the undercut recesses 18 thereof which contribute to the firm engagement between the retention pin and the amalgam or other restorative material.

Persons skilled in the art will realize that the pin may be used in a variety of orientations at various inclinations and inverted from the position shown, so it will be understood that the terms "upper" and "lower" in this description are used to describe the relative portions of the pin without limitation to their orientation with respect to a horizontal plane.

Also, it will be realized that a wide variety of structures may be devised within the broad concept of the invention, so it is emphasized that the invention is not limited solely to the disclosed embodiment but is embracing of modifications and improvements thereto which fall within the spirit of the following claims.

I claim:

1. A dental retention pin threadedly engageable in a pinhole drilled in the dentin at the base of a restoration cavity of a tooth for projecting into said cavity to assist in retaining in said cavity a subsequently inserted body of restorative material such as a dental amalgam, said pin comprising,
    a lower shaft portion having external threads of a given root diameter for engaging the dentin and a vent passage means for releasing fluid from the pinhole as the lower shaft portion is inserted therein,
    a pinhole-sealing portion at the upper end of the lower shaft portion, said pinhole-sealing portion being insertable into the pinhole and having a peripheral sealing surface for engaging the pinhole surface to prevent fluid from entering the pinhole when the lower shaft portion is fully inserted in said pinhole, and
    an upper shaft portion extending upwardly from the pinhole-sealing portion for embedment in restorative material in a restoration cavity;
    wherein the crest diameter of said threads is greater than the diameter of said pinhole sealing portion;
    wherein the diameter of the pinhole sealing portion is greater than the root diameter of said threads.

2. A method of preparing a tooth for placement of a restorative material in a restoration cavity thereof, comprising the steps of
    drilling into the dentin at the base of the restoration cavity to provide a pinhole of a given diameter for a restoration pin,
    inserting the lower end of a retention pin in the pinhole by rotating a retention pin with external threads having a crest diameter greater than said given diameter, venting fluid from the pinhole during such rotation to prevent compression of fluid in the pinhole, and cutting threads in the dentin during such rotation by moving thread-cutting edges on the pin into the wall of the pinhole, and
    sealing the pinhole during the final stages of said inserting step by moving into the pinhole a sealing portion of said pin which has a diameter substantially equal to said given diameter.

3. The method of claim 2 wherein the drilling step is performed to provide the pinhole with a bottom wall, and the inserting step is performed to move a lower end of said retention pin into contact with the bottom wall.

4. The method of claim 2 wherein the retention pin has an upper portion lying in the restoration cavity when said sealing portion is in sealing relationship to the pinhole, including the steps of placing a formable restorative material in the restoration cavity, and permitting the restorative material to harden while engaged with said retention pin.

5. The method of claim 4 wherein the drilling step is performed to provide the pinhole with a bottom wall, and the inserting step is performed to move a lower end of said retention pin into contact with the bottom wall.

* * * * *